United States Patent [19]
Tomasulo

[11] 3,994,684
[45] Nov. 30, 1976

[54] DOUBLE SHELL STERILIZER VESSEL METHOD AND APPARATUS

[75] Inventor: Frank Anthony Tomasulo, Spencerport, N.Y.

[73] Assignee: Sybron Corporation, Rochester, N.Y.

[22] Filed: June 16, 1975

[21] Appl. No.: 587,230

[52] U.S. Cl. ............................ 21/91; 21/94; 21/98; 52/656; 52/741; 220/9 R; 220/18
[51] Int. Cl.² ............................ A61L 3/00
[58] Field of Search ............... 21/91, 94, 95, 96, 97, 21/98, 92, 93, 2; 52/656, 741; 220/9 R, 18; 23/290

[56] References Cited
UNITED STATES PATENTS

| | | | |
|---|---|---|---|
| 1,409,286 | 3/1922 | Diner | 21/98 |
| 1,724,974 | 8/1929 | Sherbondy | 23/290 |
| 1,962,932 | 6/1934 | Mather, Jr. | 220/9 R X |
| 2,083,113 | 6/1937 | Bergaud | 220/9 R X |
| 2,592,705 | 4/1952 | Jewell et al. | 21/96 |
| 2,622,415 | 12/1952 | Landers et al. | 220/13 |
| 3,150,935 | 9/1964 | Matteson | 21/98 X |

FOREIGN PATENTS OR APPLICATIONS

| | | | |
|---|---|---|---|
| 1,930,910 | 12/1970 | Germany | 21/103 |

*Primary Examiner*—Morris O. Wolk
*Assistant Examiner*—Arnold Turk
*Attorney, Agent, or Firm*—Schovee & Boston

[57] ABSTRACT

In a double shell sterilizer vessel of the type having spaced-apart inner and outer shells, the improvement of an eccentric relationship between the inner and outer shells with the bottom walls of each shell in contact with each other. The eccentric double shell vessel of this invention can be: (1) pit-mounted in the floors of existing buildings with the sterilizing chamber floor level with the building floor (previous double shell vessels often could not be pit-mounted in existing buildings), and (2) floor-mounted and used with a small ramp (rather than a hydraulic lift) for sterilizer carts.

14 Claims, 3 Drawing Figures

DOUBLE SHELL STERILIZER VESSEL METHOD AND APPARATUS

BACKGROUND OF THE INVENTION

1. Field of the Invention

This invention relates to sterilizers and in particular to double sheel sterilizer vessels of the type wherein a sterilizer cart is moved into the sterilizing chamber of the inner shell.

2. Description of the Prior Art

Double shell sterilizing vessels having spaced-apart inner and outer shells are well known in the art and are mounted in one of two ways. The preferred way of mounting is to provide a pit (i.e. pit mounting) in the floor of a building when it is being built so that the sterilizing chamber floor of the inner vessel is on the same level as the external floor (that is, the building floor). When the sterilizer vessel is to be located in an existing building having floors in which, for example, a 12 inch pit cannot be provided, the vessel must be placed directly on top of the floor (i.e. floor mounting) and an expensive hydraulic lift must be placed adjacent the door into the sterilizing chamber for raising sterilizing carts having the goods to be sterilized to the level of the sterilizing chamber floor before the mobile sterilizing cart can be rolled into the chamber.

It is an object of the present invention to provide a double shell sterilizer that overcomes the above-mentioned disadvantages of prior art double shell sterilizers. It is another object of the present invention to provide a double shell sterilizer vessel having an eccentric relationship between the inner and outer shells of the sterilizer with the bottom walls of the inner and outer shells being in contact, whereby the eccentric double sterilizer vessel of the present invention can be floor-mounted and used with a small ramp without the need for a hydraulic lift, and can alternatively be pit-mounted in existing building structures which can not accommodate pit-mounting of previously known double shell sterilizer vessels. The double sheel vessel of the present invention requires a pit of much less depth (for example 6 inches) than did prior art double shell vessels.

SUMMARY OF THE PRESENT INVENTION

In a sterilizer apparatus and method comprising a double shell vessel including an outer shell and an inner shell with a sterilizing chamber in the inner shell and with each shell having top, bottom and side walls, the improvement wherein the top and side walls are spaced-apart as in the prior art, but the bottom walls are in contact with each other, whereby the sterilizer vessel can be pit-mounted even in existing building structures, because it does not require as deep a pit as does the prior art vessel, and whereby the sterilizing vessel when floor-mounted does not require a hydraulic lift but only a ramp.

BRIEF DESCRIPTION OF THE DRAWINGS

The present invention will be more fully understood by reference to the following detailed description thereof, when read is conjunction with the attached drawing, wherein like reference numerals refer to like elements and wherein.

DETAILED DESCRIPTION OF THE PREFERRED EMBODIMENT

Figure 1:
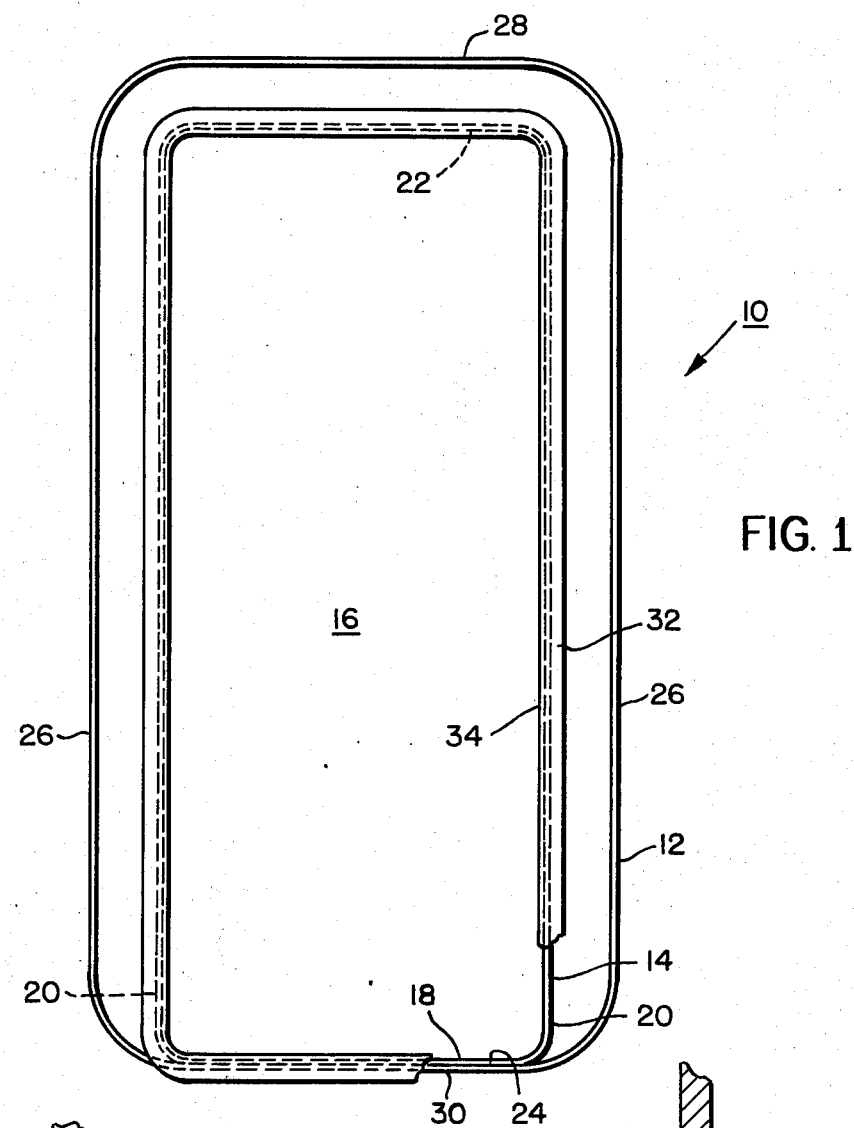
FIG. 1 is a front view of a double shell vessel of the present invention showing the eccentric relationship between the inner and outer shells.

With the reference now to the drawings, FIG. 1 shows an eccentric double shell sterilizer vessel 10 made according to the present invention and including an outer shell 12 and an inner shell 14, the inner shell 14 having a sterilizing chamber 16 and chamber floor 18 therein. The shells 12 and 14 are in eccentric relationship as shown. The inner shell 14 has side walls 20, top wall 22 and a bottom wall 24, while the outer shell 12 has side walls 26, a top wall 28, and a bottom wall 30. A flange 32 is shown attached to an edge of the inner shell 14 surrounding a door opening 34 providing an entrance into the sterilizing chamber 16. In FIG. 1, the bottom wall 24 of the inner shell 14 is in contact with the bottom wall 30 of the outer shell 12. While this is the preferred embodiment, it is not absolutely essential that these two walls be in contact, what is important is that the bottom wall 24 be moved closer to the bottom wall 30, rather than leaving the same distance therebetween as exists between the other walls of the inner and outer shells.

Figures 2, 3:
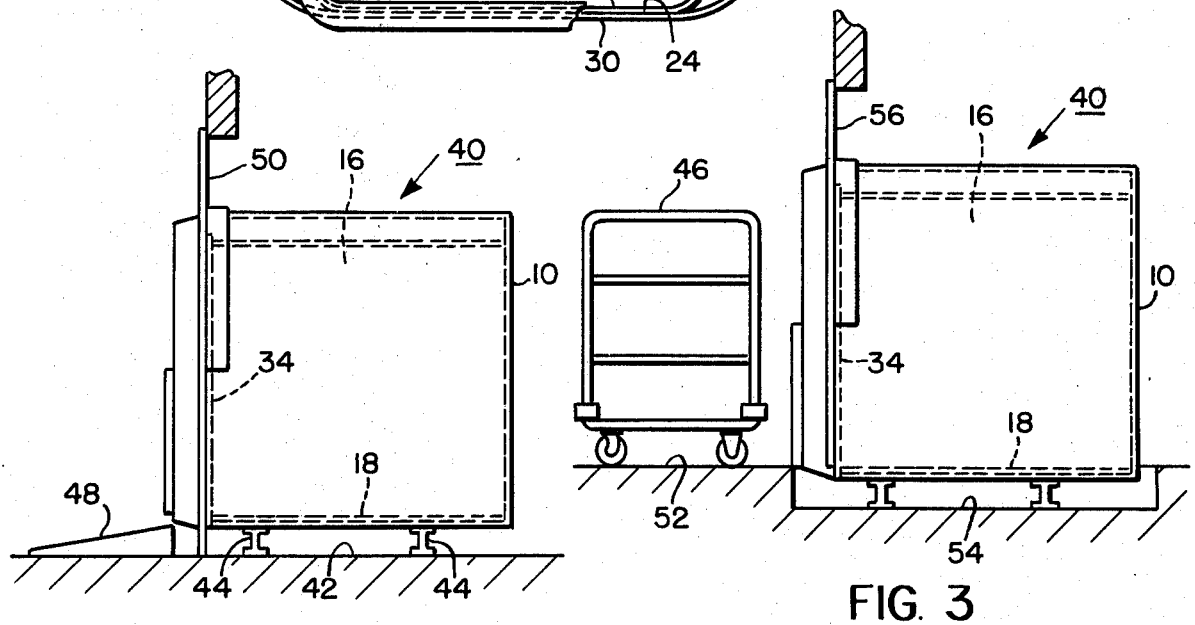
FIG. 2 is a side view of the double shell vessel of the present invention shown floor-mounted.
FIG. 3 is a side view of the double shell vessel of the present invention shown pit-mounted.

FIG. 2 shows a sterilizing apparatus 40 including the eccentric double shell vessel 10 of the present invention floor-mounted on an external floor (or building floor) 42 by means, for example, of a pair of I-beam supports 44. In order to introduce a sterilizing mobile cart 46 (see FIG. 3) into the chamber 16, it is only necessary to position a small ramp 48 on the external floor 42 adjacent the vessel 10. The vessel 10 is shown with its door opening 34 adjacent a wall 50 of the building in which the floor 42 is located.

FIG. 3 shows the sterilizing apparatus 40 including the eccentric double shell sterilizing vessel 10 of the present invention pit-mounted in an external floor 52 and located in a pit 54 such that the chamber floor 18 of the chamber 16 is substantially level with the external floor 52 so that the mobile sterilizing cart 46 can be rolled directly into the chamber 16. The opening 34 into the chamber 16 is located adjacent a wall 56 of the building.

Since sterilizer apparatuses 40 are well-known in the art, they need not be described in detail here and it will be clearly understood by one skilled in the art that the remaining equipment (in addition to the vessel 10) necessary for carrying out the sterilization process would be provided in conjunction with the vessel 10 to provide any type of sterilizing process desired, such as steam or sterilizing gas such as ethylene oxide gas.

The purpose for providing the eccentric relationship between the inner and outer shells 14 and 12, respectively, is to facilitate introducing the sterilizing cart 46 into the sterilizing chamber 16, and is particularly useful in those instances when a hydraulic lift was previously required and when pit mounting was previously impossible. According to the present invention, the eccentric double shell vessel 10 can be either floor mounted (see FIG. 2), in which case only a small ramp 48 is necessary to enable loading of the cart 46 into the sterilizing chamber 16 or it can be pit mounted (see FIG. 3) with a pit 54 formed in an external floor 52 to make the floor 18 of the chamber 16 on the same level with the external floor 52. According to the present invention, the pit 54 requires substantially less depth than would a standard pit for a standard double shell vessel in which the inner shell is spaced away from the outer shell not only between the sides and top walls but also between the bottom walls. For pit-mounting a standard double shell vessel, a pit of approximately 12 inches is required, whereas in the present invention a pit of only 6 inches is necessary, for one particular sterilizer apparatus. This is important especially in existing building structures when the existing floors can not accommodate the standard 12 inch pit and when the standard double shell vessel must be floor mounted and provided with a hydraulic lift for loading a mobile cart into the sterilizing chamber.

The invention has been described in detail with particular reference to the preferred embodiments thereof, but it will be understood that variations and modifications can be effected within the spirit and scope of the invention as described hereinabove and as defined in the appended claims. For example, other shapes of vessels 10 can be used and they can have one or more door openings, the important aspect according to the present invention being the eccentric relationship of the two shells to provide the advantages described above.

I claim:

1. An eccentric double shell sterilizer vessel having a door in a side wall thereof and including inner and outer shells wherein the bottom walls of the shells are in contact with each other and the remaining walls are spaced-apart.

2. In a sterilizer apparatus comprising a double shell vessel having a door in a side wall thereof and including an outer shell and an inner shell, said inner shell having a sterilizing chamber and a chamber floor therein, and each shell including top, bottom and side walls, the improvements wherein said top and side walls are spaced-apart from each other and said bottom walls are substantially closer to each other by a predetermined amount than are said top and side walls.

3. The apparatus according to claim 2 wherein said bottom walls are in contact with each other.

4. An apparatus including in combination with the apparatus according to claim 3, an external floor on which said sterilizer apparatus is floor-mounted and also including a ramp on which a mobile sterilizing cart can be rolled up into said sterilizing chamber.

5. An apparatus including in combination with the apparatus according to claim 3, an external floor on which said sterilizing apparatus is pit-mounted, said external floor having a pit recessed into said external floor a sufficient distance such that said external floor adjacent said pit is substantially even with said chamber floor whereby a mobile sterilizing cart can be rolled directly into said sterilizing chamber.

6. The apparatus according to claim 5 wherein said pit has a depth of approximately 6 inches.

7. The apparatus according to claim 5 wherein said external floor is one of insufficient depth to accommodate a 12 inch deep pit.

8. A method for providing access to a sterilizing chamber of a sterilizer apparatus mounted on an external floor, said sterilizer apparatus comprising a double shell vessel having a door in a side wall thereof and including an outer shell and an inner shell, said inner shell having a sterilizing chamber and a chamber floor therein, said method comprising:
   a. forming said double shell vessel with said top and side walls spaced-apart and said bottom walls substantially closer together by a predetermined amount than are said top and side walls; and
   b. forming a pit in said external floor only of sufficient depth to receive said sterilizing vessel such that said chamber floor is substantially level with said external floor, whereby access can be had to said chamber by rolling a mobile cart through said door directly into said chamber without the necessity for a ramp.

9. The method according to claim 8 wherein said double shell vessel forming step comprises placing said bottom walls in contact with each other.

10. The method according to claim 9 wherein said pit forming step comprises forming said pit approximately 6 inches deep.

11. A method for providing access to a sterilizing chamber of a sterilizer apparatus mounted on an external floor, said sterilizer apparatus comprising a double shell vessel having a door in a side wall thereof and including an outer shell and an inner shell, said inner shell having a sterilizing chamber and chamber floor therein, said method comprising:
   a. forming said double shell vessel with said top and side walls spaced-apart and said bottom walls substantially closer together by a predetermined amount than are said top and side walls;
   b. placing said double shell vessel directly on top of said external floor; and
   c. positioning a ramp on said external floor adjacent said vessel for use in rolling a mobile cart up into said sterilizing chamber.

12. The method according to claim 11 wherein said forming step comprises placing said bottom walls in contact with each other.

13. The method according to claim 8 including the step of rolling a mobile cart directly into said chamber through said door without a ramp.

14. The method according to claim 12 including the step of rolling a mobile cart up said ramp and into said chamber through said door.

* * * * *